United States Patent [19]

Colvin et al.

[11] Patent Number: 4,538,002

[45] Date of Patent: Aug. 27, 1985

[54] PROCESS FOR THE PRODUCTION OF HYDROXYANISOLE AND ALKYLATED HYDROXYANISOLES

[75] Inventors: Howard A. Colvin, Akron; Joel Muse, Jr., Kent; William S. Hollingshead, Cuyahoga Falls, all of Ohio

[73] Assignee: The Goodyear Tire & Rubber Company, Akron, Ohio

[21] Appl. No.: 649,231

[22] Filed: Sep. 10, 1984

[51] Int. Cl.$^3$ .................. C07C 41/18; C07C 41/16; C07C 37/00; C07C 39/19

[52] U.S. Cl. ................... 568/650; 568/658; 568/782

[58] Field of Search ............ 568/782, 658, 650

[56] References Cited

U.S. PATENT DOCUMENTS

| | | | |
|---|---|---|---|
| 2,908,718 | 10/1959 | Rosenwald | 568/650 |
| 4,328,361 | 5/1982 | Dai | 568/650 X |
| 4,346,249 | 8/1982 | Krabbenhoft | 568/782 |

OTHER PUBLICATIONS

Balandin et al., Jour. Applied Chem., 12:ii159, (1962).
Corson et al., Jour. Org. Chem., vol. 23, (1958), 544–549.

Primary Examiner—Bernard Helfin
Attorney, Agent, or Firm—D. O. Nickey

[57] ABSTRACT

There is disclosed a process for the production of alkylated hydroxyanisoles which consists of dehydrogenating para-isopropylphenol to para-isopropenylphenol which is then reacted with a methylating agent to yield para-isopropenylanisole which is then treated with acidic hydrogen peroxide to yield para-hydroxyanisole which is then treated with an alkylating agent to yield the alkylated hydroxyanisole. The process of this invention is especially useful for the synthesis of the food preservative butylated hydroxyanisole (BHA).

15 Claims, No Drawings

PROCESS FOR THE PRODUCTION OF HYDROXYANISOLE AND ALKYLATED HYDROXYANISOLES

TECHNICAL FIELD

This invention relates to a novel method of producing hydroxyanisole and alkylated hydroxyanisoles. More specifically, this invention is concerned with the production of butylated hydroxyanisole (BHA) which is useful as a food stabilizer.

BACKGROUND ART

Butylated hydroxyanisole or 2-butyl-4-methoxyphenol is an accepted antioxidant which has found commercial use in the food industry. Generally, butylated hydroxyanisole is in the form of a white crystal with a melting point of about 64° C. and is insoluble in water. In addition, hydroxyanisole and/or BHA have found use as starting materials for the manufacture of antioxidants, pharmaceuticals, plasticizers, dye stuffs, and as a stabilizer for certain hydrocarbons.

Heretofore, numerous synthetic routes have been used to produce BHA or alkylated hydroxyanisoles. For example, U.S. Pat. No. 2,887,515 teaches the preparation of BHA by alkylation of tertiary butyl hydroquinone with dimethyl sulfate. The tertiary butyl hydroquinone is prepared from hydroquinone as taught by U.S. Pat. No. 2,722,556. Alternatively, hydroquinone can be methylated to give p-hydroxyanisole as taught in British Pat. No. 1,277,186 or British Pat. No. 1,450,296 and alkylated with isobutylene to give BHA. Both of the above processes require expensive hydroquinone as a starting material and require a selective methylation. The present invention provides a process for the production of alkylated hydroxyanisoles which utilizes as a starting material a waste stream from a process for the production of hydroquinone. In addition, the instant invention is directed to a process that overcomes the selectivity problems associated with processes used heretofore.

DISCLOSURE OF THE INVENTION

There is disclosed a process for the production of alkylated hydroxyanisoles which consists essentially of: (A) dehydrogenating para-isopropylphenol in the vapor phase by passing para-isopropylphenol over a catalyst consisting of copper oxide (CuO) and chromium oxide ($Cr_2O_3$), the weight ratio of $Cr_2O_3$ to CuO ranging from 2:1 to 1:1; at a temperature from 350° to 650° C. and at an LHSV of from 1.0 to 3.0 to yield para-isopropenylphenol; (B) reacting para-isopropenylphenol with a methylating agent to yield para-isopropenylanisole; (C) reacting para-isopropenylanisole with hydrogen peroxide in the presence of a mineral acid and a solvent to yield para-hydroxyanisole; and (D) reacting para-hydroxyanisole with an alkylating agent wherein the alkyl radical is from 3 to 6 carbon atoms to yield the alkylated hydroxyanisole.

There is also disclosed a process for the production of hydroxyanisole which consists essentially of: (A) dehydrogenating para-isopropylphenol in the vapor phase by passing para-isopropylphenol over a catalyst consisting of copper oxide (CuO) and chromium oxide ($Cr_2O_3$), the weight ratio of $Cr_2O_3$ to CuO ranging from 2:1 to 1:1; at a temperature from 350° to 650° C. and at an LHSV of from 1.0 to 3.0 to yield para-isopropenylphenol; (B) reacting para-isopropenylphenol with a methylating agent to yield para-isopropenylanisole; and (C) reacting para-isopropenylanisole with hydrogen peroxide in the presence of a mineral acid and a solvent to yield para-hydroxyanisole.

The weight ratio of $Cr_2O_3$ to CuO can range from 2:1 to 1:1 with a more preferred ratio being 1.25:1 to 1.5:1. The temperature may range from 350° C. to 650° C. for the dehydrogenation reaction with from 500° to 600° C. being preferred. The LHSV is preferably from 2.5 to 3.0.

Methylating agents useful in the instant invention include methyl halides, methanol and dimethylsulfate. Representative of the mineral acids useful in the instant invention are sulfuric, hydrochloric, hydrobromic and perchloric.

Representative alcohols which are useful as a solvent in the instant invention are those alcohols of 3 to 10 carbon atoms; however, the skilled artisan would realize that any solvent for the reaction mixture which is inert would be suitable.

Representative of the alkylating agents useful in the instant invention are isobutylene, propylene, isoamylene and hexene.

BEST MODE OF THE INVENTION

The starting material for the process of the instant invention is obtained from a waste stream from a process for the production of hydroquinone. Benzene or cumene is alkylated with propylene according to known technology to produce primarily the meta- and paraisomers of diisopropylbenzene. The para isomer is oxidized to the dihydroperoxide, and after isolation is subsequently contacted with an acid to effect the cleavage to hydroquinone. One by-product of that process is para-isopropylphenol. This by-product is useful for the production of alkylated hydroxyanisoles through the process of the present invention. Heretofore, the starting material para-isopropylphenol was burned for fuel value. The initial step of the instant invention consists of preparing paraisopropenylphenol by the catalytic dehydrogenation of para-isopropylphenol.

EXPERIMENT 1

Preparation of Para-Isopropenylphenol from Para-Isopropylphenol

This reaction was carried out using a tubular stainless steel reactor approximately 1.25 cm by 10 cm that was equipped with heaters for the reaction zone as well as a preheater zone to heat the feed prior to contact with the catalyst. The reaction products were analyzed by gas chromatography to determine the extent of the dehydrogenation and the selectivity to para-isopropenylphenol. The para-isopropylphenol feed was diluted with toluene to facilitate handling, and the toluene also served as an inert carrier for the isopropenylphenol from the reaction zone.

One skilled in the art of chemical engineering will realize that on a commercial scale, a different catalyst size and shape might be more appropriate. The process of the present invention is intended to include such obvious modifications.

TABLE I

Dehydrogenation of p-Isopropylphenol to p-Isopropenylphenol with Copper Chromite 37% CuO, 53% $Cr_2O_3$ 600° C.

| | Reactor Feed | LHSV* | Catalyst Size | Conversion | Selectivity |
|---|---|---|---|---|---|
| 1. | 19.15% PIPP 80.85% toluene | 1.2 | Pellets ⅛" × ⅛" | 42.7% 50.5% 41.7% | 89% 100% 100% |
| 2. | 46.8% PIPP 53.2% toluene | 2.9 | Pellets ⅛" × ⅛" | 29.9 40.0 41.3 | 91.4 99.6 87.9 |
| 3. | 46.8% PIPP 53.2% toluene | 8.9 | Pellets ⅛" × ⅛" | 11.0% | 93.2 |
| 4. | 46.8% PIPP 53.2% toluene | 2.6 | 8–16 mesh | 63.8% | 97.4 |
| 5. | 53.0% PIPP 47.0% toluene | 3.4 | 8–16 mesh | 58.8 59.3 | 98.8 98.5 |

* $\frac{\text{Volume of Liquid Reactant}}{\text{Volume of Catalyst Bed}}$ /hr

It has been determined that iron oxides are poor catalysts. The conversions range from 0 to about 20%. In some reactions the reaction product contained phenol, para-cresol and para-ethylphenol. The use of iron oxide on alumina was only slightly better. Conversions of up to 70% were achieved; however, selectivity was still poor as there was formation of undesirable phenols.

The use of chromia on aluminum and palladium on carbon gave moderate conversions, but was poor in selectivity to isopropenylphenol.

The use of copper chromite catalysts gave both very good selectivity and good conversions.

The results from Table I show five different reactor feeds and catalyst sizes. Nos. 1, 2 and 3 from Table I show the effect of flow rate and indicate that an LHSV in the range of about 3 or less seems to be most appropriate. The catalyst form was pellets in the size of 0.3 by 0.6 cm, and these were cut in half and used in Experiments 1, 2 and 3. A catalyst size slightly larger than the 8–16 mesh is not as effective as the crushed and sieved 8–16 mesh size used in all the other Experiments. This data indicates that a catalyst consisting of CuO and $Cr_2O_3$ at a weight ratio of $Cr_2O_3$ to CuO ranging from 2:1 to 1:1 to be the most appropriate to efficiently effect the dehydrogenation of para-isopropylphenol to para-isopropenylphenol.

EXPERIMENT 2

Preparation of Para-Isopropenylanisole from Para-Isopropenylphenol—Methyl Iodide as a Methylating Agent A two-liter reaction flask was charged with 375 mls of water, 18.25 gms of sodium hydroxide, 125 mls of saturated sodium chloride, 50 gms of para-isopropenylphenol, 450 cc of methylene chloride, 7.5 gms of tetrabutylammoniumbromide, and 35 mls of methyl iodide. The reaction flask was flushed with nitrogen, and the mixture was stirred overnight. The phases were separated, and the aqueous phase was washed with methylene chloride. The combined organic layers were washed with 5% sodium hydroxide and saturated sodium chloride. The solution was dried over sodium sulfate. The methylene chloride was removed by distillation, and 400 mls of diethyl ether was added to precipitate the phase transfer catalyst. After filtration, the ether was stripped and the residue was distilled to give 25 gms of para-isopropenylanisole for a yield of 45%.

EXPERIMENT 3

Preparation of Para-Isopropenylanisole from Para-Isopropenylphenol—Dimethyl Sulfate as a Methylating Agent Into a 250 ml three-neck flask equipped with a magnetic stirrer, pressure equalizing dropping funnel with a nitrogen inlet and thermometer was placed 70 cc of water and 3.05 gm of sodium hydroxide. Dimethyl sulfate (9.2 gm, 73 mmole) was charged to the dropping funnel, and the flask was flushed with nitrogen. p-Isopropenylphenol (9.8 gm, 73 mmole) was added to the sodium hydroxide solution, and the flask was closed and cooled to 10° C. with an ice bath. The dimethyl sulfate was added over one minute. The reaction mixture was stirred for 15 minutes at 10° C. and heated to 70° C. for fifty minutes. The mixture was cooled and extracted with ether. The ether extract was washed with saturated sodium chloride solution and dried with sodium sulfate. Evaporation of the solvent left 7.21 gm (yield of 67%) of the desired product as an oil which crystallized on standing.

EXPERIMENT 4

Preparation of Para-Hydroxyanisole from Para-Isopropenylanisole

Into a 250 ml reaction flask was charged 1 gm of sulfuric acid, 4.6 gms of 50% $H_2O_2$ and 30 cc of octanol. To this was slowly added 10 gms of para-isopropenylanisole in 20 cc of octanol. The reaction mixture was heated to about 40° C., but within 15 minutes the mixture has exothermed to about 90° C. The mixture was cooled to 40° C. and kept at that tempeature for 4 hours. A gas chromatographic analysis indicated that the crude product consisted of 93.5% para-methoxyphenol and 6.5 para-isopropenylanisole. The mixture was washed with caustic, extracted with ether, and the ether was evaporated to leave 8.3 gms of the material which was 91% para-methoxyphenol and 9% 1-octanol or 89% yield.

EXPERIMENT 5

Preparation of BHA from Para-Hydroxyanisole

Para-hydroxyanisole is alkylated with a gamma alumina catalyst. The catalyst is prepared by the general steps of digesting aluminum metal cuttings with hydrogen chloride to form an alumina sol, then co-mixing hexamethylene-tetramine therewith and dropping the sol into an oil bath wherein the droplets form into spheres which are afterward washed and dried in a stream of air at about 315° C. and calcined at about 530° C. for about 3 hours.

The catalyst is utilized for the alkylation of hydroxyanisole and isobutylene by passing the reactants upward through a fixed bed of catalyst at a pressure of 962 kPa using a mole ratio of para-hydroxyanisole to isobutylene of 10:1. 100 gms of para-hydroxyanisole is used in the run. The reaction is carried out at 178° C. Conversion of isobutylene is greater than 95%, and the alkylated product consists only of 3-tert-butyl para-hydroxyanisole.

INDUSTRIAL APPLICABILITY

The prior art methods for producing BHA result in the intermediate production of diethers which would require separation prior to further reaction.

The instant invention overcomes this problem in that diethers are not formed. Thus, the reaction is very selective. In addition, the instant invention uses a waste stream as the starting material and not the heretofore used hydroquinone.

Having described the invention in such detail as to allow one skilled in the art to perform the same without undue experimentation, the applicants claim the following.

We claim:

1. A process for the production of alkylated hydroxyanisoles which consists essentially of:
   (A) dehydrogenating para-isopropylphenol in the vapor phase by passing para-isopropylphenol over a catalyst consisting of CuO and $Cr_2O_3$, the weight ratio of $Cr_2O_3$ to CuO ranging from 2:1 to 1:1, at a temperature from 350° C. to 650° C. and at an LHSV of from 1.0 to 3.0 to yield para-isopropenylphenol;
   (B) reacting para-isopropenylphenol with a methylating agent to yield para-isopropenylanisole;
   (C) reacting para-isopropenylnisole with hydrogen peroxide in the presence of a mineral acid and a solvent to yield para- hydroxyanisole;
   (D) reacting para-hydroxyanisole with an alkylating agent wherein the alkyl radical is from 3 to 6 carbon atoms to yield the alkylated hydroxyanisole.

2. A process according to claim one wherein the weight ratio of $Cr_2O_3$ to CuO is 1.25:1 to 1.5:1.

3. A process according to claim 1 wherein the dehydrogenation reaction is conducted from 500° to 600° C.

4. A process according to claim 1 wherein the LHSV is from 2.5 to 3.0.

5. A process according to claim 1 wherein the methylating agent is selected from the group consisting of methyl halides, methanol and dimethylsulfate.

6. A process according to claim 1 wherein the mineral acid is selected from the group consisting of sulfuric, hydrochloric, hydrobromic and perchloric.

7. A process according to claim 1 wherein the solvent for the reaction of hydrogen peroxide with isopropenylanisole is an alcohol of 4 to 10 carbon atoms.

8. A process according to claim 1 wherein the alkylating agent is selected from the group consisting of isobutylene, propylene, isoamylene and hexene.

9. A process for the production of hydroxyanisole which comprises:
   (A) dehydrogenating para-isopropylphenol in the vapor phase by passing para-isopropylphenol over a catalyst consisting of CuO and $Cr_2O_3$, the weight ratio of $Cr_2O_3$ to CuO ranging from 2:1 to 1:1, at a temperature from 350° C. to 650° C. and at an LHSV of from 1.0 to 3.0 to yield para-isopropenylphenol;
   (B) reacting para-isopropenylphenol with a methylating agent to yield para-isopropenylanisole; and
   (C) reacting para-isopropenylanisole with hydrogen peroxide in the presence of a mineral acid and a solvent to yield para- hydroxyanisole.

10. A process according to claim 9 wherein the weight ratio of $Cr_2O_3$ to CuO is 1.25:1 to 1.5:1.

11. A process according to claim 9 wherein the dehydrogenation reaction is conducted from 500° to 600° C.

12. A process according to claim 9 wherein the LHSV is from 2.5 to 3.0

13. A process according to claim 9 wherein the methylating agent is selected from the group consisting of methyl halides, methanol and dimethylsulfate.

14. A process according to claim 9 wherein the mineral acid is selected from the group consisting of sulfuric, hydrochloric, hydrobromic and perchloric.

15. A process according to claim 9 wherein the solvent for the reaction of hydrogen peroxide with isopropenylanisole is an alcohol of 4 to 10 carbon atoms.

* * * * *

UNITED STATES PATENT AND TRADEMARK OFFICE
CERTIFICATE OF CORRECTION

PATENT NO. : 4,538,002
DATED : August 27, 1985
INVENTOR(S) : Colvin et al

It is certified that error appears in the above-identified patent and that said Letters Patent is hereby corrected as shown below:

Column 2, line 6, delete "Crhd $2O_3$" and replace therewith --$Cr_2O_3$--.

Column 2, line 44, delete "paraisopropenylphenol" and replace therewith --para-isopropenylphenol--.

Column 5, line 24, delete "para-isopropenylnisole" and replace therewith --para-isopropenylanisole--.

Signed and Sealed this

Third Day of June 1986

[SEAL]

Attest:

DONALD J. QUIGG

Attesting Officer

Commissioner of Patents and Trademarks